United States Patent
Cohen

[11] 3,944,596
[45] Mar. 16, 1976

[54] PROCESS FOR THE PREPARATION OF 3-MONO-ALKYL AND 3,6-DIALKYL-RESORCYLIC ESTERS

[75] Inventor: Amnon Mordechai Cohen, Amersfoort, Netherlands

[73] Assignee: P.F.W. Beheer B.V., Amersfoort, Netherlands

[22] Filed: Nov. 23, 1973

[21] Appl. No.: 418,796

[30] Foreign Application Priority Data
Nov. 29, 1972 United Kingdom............... 55067/72
June 22, 1973 United Kingdom............... 29647/72

[52] U.S. Cl. ............................................. 260/473 S
[51] Int. Cl.² .......................................... C07C 69/84
[58] Field of Search .............................. 260/473 S

[56] References Cited
UNITED STATES PATENTS
| | | | |
|---|---|---|---|
| 2,311,507 | 2/1943 | Arthur | 260/239.3 R |
| 3,634,491 | 1/1972 | Grossman et al. | 260/473 S |
| 3,729,519 | 4/1973 | Brossi et al. | 260/473 S |

FOREIGN PATENTS OR APPLICATIONS
902,636   6/1972   Canada

OTHER PUBLICATIONS
House, "Modern Synthetic Reactions", W. A. Benjamin Inc. (1972) pp. 432–435.

*Primary Examiner*—John F. Terapane

[57] ABSTRACT

Mono- and dialkyl-resorcylic esters of the general formula

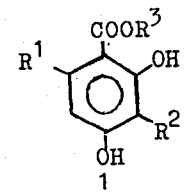

wherein $R^1$ is hydrogen or an alkyl radical containing up to three carbon atoms, $R^2$ represents an alkyl radical (preferably a lower alkyl radical such as methyl or ethyl) and $R^3$ represents methyl or ethyl, are prepared by reacting the corresponding dihydroresorcylic esters having the general formula

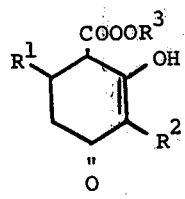 to 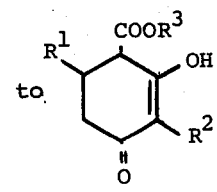

with organic N-haloamides. Halocaprolactams, and especially N-chlorocaprolactam, are preferred reactants.

15 Claims, 1 Drawing Figure

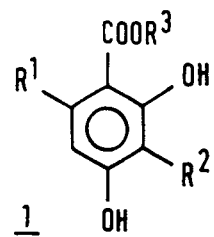
<u>A</u>
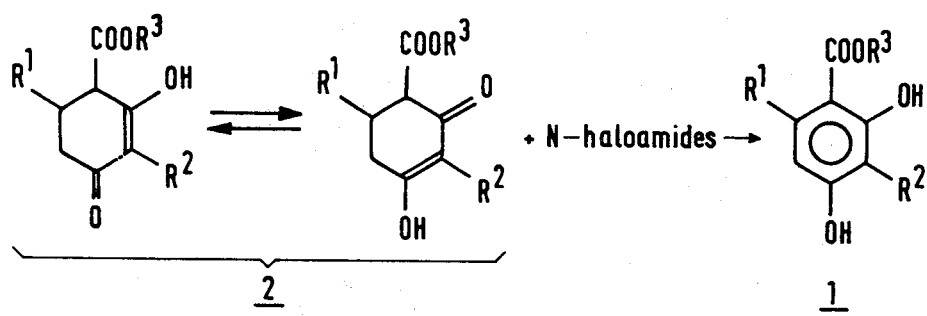
<u>B</u>
1) $R^2CH_2CCH_2COOR^3$ + $R^1CH=CHCOOR^3$
   $\quad\quad\quad\|$
   $\quad\quad\quad O$
2) $R^1CH=CHCCH_2R^2$ + $CH_2(COOR^3)_2$ $\xrightarrow{NaOR^3}$ <u>2</u>
   $\quad\quad\quad\quad\|\quad\quad\quad\quad\quad\quad\quad R^3OH$
   $\quad\quad\quad\quad O$
$\xrightarrow{\underset{R^3OH}{Na\,OR^3}}$ <u>2</u>
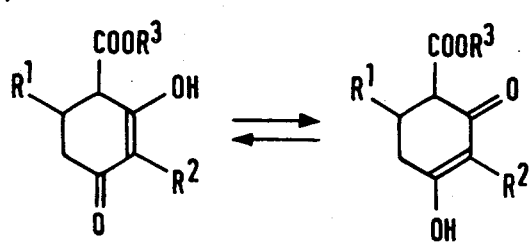

PROCESS FOR THE PREPARATION OF 3-MONO-ALKYL AND 3,6-DIALKYL-RESORCYLIC ESTERS

This invention relates to the preparation of mono- and dialkyl-resorcylic esters of the general formula 1 wherein $R^1$ is hydrogen or an alkyl radical containing up to 3 carbon atoms, $R^2$ represents an alkyl radical having up to 3 carbon atoms, preferably a methyl or ethyl radical and $R^3$ represents methyl or ethyl. The resorcylates of formula 1 are valuable in perfumery. Among them are highly prized oak moss fragrance materials such as Pat. No. 3,6-dimethylresorcylate and methyl 3-ethyl-6-methyl-resorcylate. While various synthetic methods are known for the preparation of resorcylic esters, such methods are generally uneconomic. For example, a method described by A. Sonn, Ber. 62B, 3012 (1929), involves utilisation of the expensive palladium for the aromatization of dihydroresorcylic esters. A further method described by A. Sonn (loc.cit.), involves converting 3,6-dimethyl-5-bromoresorcylic esters into the corresponding resorcylates by catalytic hydrogenolysis over a palladium catalyst. Another method which employs chlorine for the aromatization of 3,6-dialkyl-dihydroresorcylates (U.S. Pat.No. 3,634,491) affords, in practice, impure reaction products in rather poor yields (17–50%). Purification of these reaction products can be achieved only at a considerable additional loss of material. With other halogens, such as for instance bromine, this reaction fails completely.

It has now been found that very pure resorcylic esters of the class above designated can be prepared in high yield (up to 85%), in a technically very simple and commercially feasible manner.

In general the process of this invention may be represented schematically by equation A wherein $R^1$ represents a hydrogen atom or an alkyl radical containing up to 3 carbon atoms; $R^2$ represents an alkyl radical having up to 3 carbon atoms, preferably a methyl or ethyl radical and $R^3$ represents methyl or ethyl.

Most of the intermediate dihydroresorcylic esters represented by the tautomeric formulae 2 are known compounds (cf. A. Sonn, Ber. 62B, 3012 (1929); U.S. Pat. No. 3,634,491). As far as they are new, known methods can be employed for their preparation, as is illustrated by reaction scheme B, wherein $R^1$, $R^2$ and $R^3$ have the same meaning as above.

Any organic N-haloamide can succesfully be utilized as an aromatizing agent in the process of this invention. More specifically suitable N-haloamides include aliphatic amides such as N-chloro and N-bromacetamide; aromatic amides such as N-bromobenzamide and N-chloroacetanilide; cyclic amides such as N-bromo and N-chlorocaprolactam and cyclic imides such as N-chloro and N-bromosuccinimide, the corresponding phthalimides and N,N-dihalohydantoins. In view of the large variety in mode of reaction usually entered into by the various N-haloamides mentioned above - which encompasses allylic bromination or chlorination, addition to double bonds, aromatic substitution (i.e. bromination or chlorination of the aromatic nucleus) etc. (see "Houben Weyl" Methoden der Organischen Chemie, Vol. 5/3 p. 796–811 (1962) - the manner, and even more, the unexpected uniformity and high selectivity of their reaction with the different mono and dialkyl-resorcylates is quite surprising, the more so as both the starting dihydroresorcylates and the aromatic products have various functional groups and substituents which are known to be, as a rule, very reactive towards some and in certain cases towards all of the N-haloamides cited above, depending on the functional group.

Taking into account various factors such as availability and price of the N-haloamides on one hand and yield and technological feasibility of the aromatization process on the other, the halocaprolactams and especially N-chlorocaprolactam is the aromatization agent of choice. Aromatizations of various mono- and dialkyl-dihydroresorcylates by N-chloro-caprolactam proceed in all cases very smoothly affording the corresponding resorcylates in very high state of purity and in uniformly high yields, varying in most cases within the narrow margin of 80% to 85%. It may be of interest to note that unlike some of the other haloamides cited above, the only type of reaction reported in the chemical literature for N-chlorocaprolactam is its thermal rearrangement to α-chlorocaprolactam (U.S. Pat. No. 3,045,009).

All of the N-haloamides cited above are known compounds which are either commercially available or can very easily be made from their corresponding amides.

The process of this invention is suitably carried out by dissolving or suspending the dihydroresorcylic ester and the N-haloamide in a solvent such as benzene, carbon tetrachloride or water and heating the reaction mixture for several hours. The solid reaction products are recovered and isolated by simple conventional techniques such as filtration of the reaction mixture or selective extraction. Although a wide variety of both polar and non-polar solvents may be used in the process of this invention, it is preferred to use hydrocarbons, especially aromatic hydrocarbons, such as benzene, or chlorinated hydrocarbons, such as carbon tetrachloride. In using N-haloamides as aromatizing agents there is no preference between a polar or a non-polar solvent. The reaction proceeds as smoothly, and with practically the same yields, in a non-polar solvent, such as benzene or carbon tetrachloride, as in a highly polar solvent, such as water. The reaction temperature is dependent on the solvent and the nature of the reactants. However, the reaction is usually carried out at the reflux temperature of the reaction solvent since lower temperatures are in general of no practical advantage, mainly resulting in longer reaction times. The reaction time depends on various factors such as reaction temperature, solvent and the nature of the reactants. As a rule, aromatizations conducted at reflux temperatures with N-chloroamides require considerably shorter reaction times (1–12 hours) than those conducted with N-bromoamides (up to 24 hours).

In order to illustrate this invention further, but without limiting the same, the following examples are given:

EXAMPLE 1

Methyl 3,6-dimethyl-dihydroresorcylate

In a 4-L three-necked flask fitted with a mechanical stirrer, a dropping funnel, a thermometer and a reflux condenser protected by a calcium chloride drying tube, is placed a solution of 200 g of sodium methoxide in 1400 ml of methanol. To the stirred solution is added, at room temperature, 313 g of dimethyl malonate over a period of 15 minutes. The reaction mixture is stirred for an additional 15 minutes and 272,5 g of a mixture of 4-hexen-3-one (56%) and 5-chlorohexan-3-one (44%) (prepared from propene and propionyl chloride, according to the method of R. B. Woodward et al, J.AM.-Chem.Soc., 74, 4239 (1952); b.p. 65°–79°C/60 mm) is added rapidly. The reaction mixture is stirred at reflux temperature for 9 hours. The solvent is distilled off under reduced pressure and the residue is dissolved in water. The aqueous solution is acidified with dilute hydrochloric acid. The solid product is filtered off and washed thoroughly with water, yielding 402 g (86%) of methyl 3,6-dimethyl-dihydroresorcylate, m.p. 156°–157°C.

EXAMPLE 2

Methyl 3,6-dimethyl-resorcylate

In a 1-L round-bottomed flask fitted with a reflux condenser and a calcium chloride drying tube, are placed 99 g of methyl 3,6-dimethyl-dihydroresorcylate, 96 g of N-bromocaprolactam (B. Taub and J. B. Hino, J. Org.Chem. 25, 263 (1960) and 200 ml of carbon tetrachloride. The reaction mixture is refluxed for 24 hours and then cooled to room temperature. The reaction mixture is stirred for several minutes with 500 ml. of water, cooled to 0°C and filtered. The solid product is washed with 20 ml of cold carbon tetrachloride and then with water. At this stage the product contains 10–20% of co-precipitated caprolactam and traces of unreacted methyl 3,6-dimethyl-dihydroresorcylate which are removed in the following manner. The product is dissolved in 300 ml of boiling methanol; 1 L of 2% potassium bicarbonate solution is added slowly with stirring to the warm methanolic solution effecting reprecipitation of the pure reaction product. The mixture is cooled to 0°C and filtered. The product is washed thoroughly with water and dried, yielding 79.5 g (81%) of methyl 3,6-dimethyl resorcylate (identified by NMR, IR and mass spectral analysis) m.p. 139.5° – 140.5°C.

EXAMPLE 3

Methyl 3,6-dimethyl-resorcylate

In a 0.5-L round bottomed flask fitted with a reflux condenser and a calcium chloride drying tube, is placed a solution of 49.5 g of methyl 3,6-dimethyl-dihydroresorcylate and 48 g of N-bromocaprolactam in 250 ml of benzene. The reaction mixture is refluxed for 24 hours, then cooled to 30°C, transferred to a separatory funnel and washed successively with 200 ml. of water, 500 ml of 0.2 molar sodium carbonate solution and 200 ml of water. The organic layer is then cooled to 5°C and extracted with 750 ml of cold 0.4N sodium hydroxide solution and 250 ml of cold water. The combined aqueous solutions are acidified with a slight excess of 15% hydrochloric acid, added slowly enough to ensure precipitation of a finely divided product. The temperature is maintained at 0°C throughout the acidification. The solid product is filtered off, washed thoroughly with water and dried, yielding 27 g (75%) of methyl 3,6-dimethyl-resorcylate. M.p. 139°–140°C.

EXAMPLE 4

Methyl 3,6-dimethyl-resorcylate

In a 0.5-L three-necked flask fitted with a mechanical stirrer, a thermometer and a reflux condenser, protected by a calcium chloride drying tube, are placed a solution of 36.9 g of N-chlorocaprolactam (H. Beyer and J. Korosi, Ber. 94, 480 (1961)) in 250 ml of benzene and 49.5 g of methyl 3,6-dimethyl-dihydroresorcylate. The reaction mixture is warmed up slowly with stirring until the appearance of a sudden exothermic reaction (usually occurring at 70°–75°C) at which point the heating bath is removed. After the vigorous reaction has subsided, the heating bath is replaced and the reaction mixture is stirred at reflux temperature for an additional 3.5 hours. The reaction mixture is then cooled to 30°C and worked up in the same manner as described in Example 3. There is obtained 39.5 g (80%) of methyl 3,6-dimethyl-resorcylate melting at 140°–141°C.

EXAMPLE 5

Methyl 3,6-dimethyl-resorcylate

In a 0.5-L three-necked flask fitted with a mechanical stirrer and a reflux condenser are placed 9.9 g of methyl 3,6-dimethyl-dihydroresorcylate, 7.4 g of N-chlorocaprolactam and 100 ml of water. The reaction mixture is stirred at room temperature for 5 hours and then at 50°C for an additional 2 days. The reaction mixture is cooled to 0°C and filtered. The solid product is dissolved in 10 ml of methanol. The methanolic solution is then added slowly with stirring to 100 ml of a 5% potassium bicarbonate solution, effecting reprecipitation of the pure reaction product. The mixture is cooled to 0°C and filtered. The product is washed thoroughly with water and dried, yielding 7.8 g (80%) of methyl 3,6-dimethyl-resorcylate melting at 140°–141°C.

EXAMPLE 6

Methyl 3,6-dimethyl-resorcylate

In a 0.5-L three-necked flask fitted with a mechanical stirrer and a reflux condenser, protected by a calcium chloride drying tube, are placed 19.8 g of methyl 3,6-dimethyl-dihydroresorcylate, 9.4 g of N-chloroacetamide (K. J. P. Orton and A. E. Bradfield, J.Chem.Soc. 1927, 986) and 100 ml of benzene. The reaction mixture is refluxed with stirring for 3,5 hours and then cooled to room temperature. The reaction mixture is stirred for several minutes with 200 ml of water cooled to 5°C and filtered. The product is washed with water, 5% sodium carbonate solution and finally with water, yielding 14 g (71%) of methyl 3,6-dimethyl-resorcylate.

EXAMPLE 7

Methyl 3,6-dimethyl-resorcylate.

In a 0.5-L three-necked flask fitted with a mechanical stirrer and a reflux condenser protected by a calcium chloride drying tube, are placed 19.8 g of methyl 3,6-dimethyl-dihydroresorcylate, 17.8 g of freshly recrystallized N-bromosuccinimide, 0.1 g of benzoyl peroxide and 100 ml of benzene. The reaction mixture is stirred at reflux temperature for 24 hours. Approximately half of the solvent is distilled off and the residue is stirred for several minutes with 200 ml of water, cooled to 5°C and filtered. The product is washed thoroughly with water, 5% sodium carbonate solution and finally with water, yielding 14.3 g (72%) of methyl 3,6-dimethyl-resorcylate.

EXAMPLE 8

Example 7 is repeated with omission of benzoyl peroxide. Methyl 3,6-dimethyl-resorcylate is obtained in a lower yield (61%).

EXAMPLE 9

Methyl 3,6-dimethyl-resorcylate

In a 250-ml round-bottomed flask fitted with a reflux condenser, protected by a calcium chloride drying tube, are placed 19.8 g of methyl 3,6-dimethyl-dihydroresorcylate, 13.4 g of N-chlorosuccinimide and 100 ml of benzene. The reaction mixture is refluxed for 8 hours and then worked up in the same manner as described in Example 7. There is obtained 12.5 g (64%) of methyl 3,6-dimethyl-resorcylate.

EXAMPLE 10

Methyl 3,6-dimethyl-resorcylate

In a 250-ml three-necked flask fitted with a mechanical stirrer, a thermometer and a reflux condenser protected by a calcium chloride drying tube, is placed a solution of 13.6 g of N-chloroacetanilide (C. D. Barney and C. W. Porter, J.Am.Chem.Soc. 52, 1721 (1930) in 80 ml of benzene. To the stirred solution is added, in one portion, 15.8 g of methyl 3,6-dimethyl-dihydroresorcylate. The reaction starts at once with a considerable evolution of heat. After the reaction subsides, the reaction mixture is refluxed for 3 hours and then worked up in the same manner as described in Example 3. There is obtained 10.7 g (68%) of methyl 3,6-dimethyl-resorcylate.

EXAMPLE 11

Methyl 3,6-dimethyl-resorcylate

In a 250-ml three-necked flask fitted with a mechanical stirrer and a reflux condenser protected by a calcium chloride drying tube, are placed 9.9 g of methyl 3,6-dimethyl-dihydroresorcylate, 10 g of N-bromobenzamide (British Pat. No. 928,897) and 50 ml of benzene. The reaction mixture is refluxed for stirring for 2 hours, cooled to room temperature, diluted with ether and filtered. The filtrate is transferred to a separatory funnel and washed successively with water, 0.2 molar sodium carbonate solution and again with water. The organic layer is then cooled to 5°C and extracted with cold 0.4N sodium hydroxide solution. The aqueous solution is acidified with a slight excess of 15% hydrochloric acid. The temperature is maintained at 0°C throughout the acidification. The solid product is filtered off, washed thoroughly with water and dried, yielding 7.1 g (72%) of methyl 3,6-dimethyl-resorcylate.

EXAMPLE 12

Example 11 is repeated with addition of 0.05 g of benzoyl peroxide. Methyl 3,6-dimethyl-resorcylate is obtained in a somewhat higher yield (75,5%).

EXAMPLE 13

Methyl 3,6-dimethyl-resorcylate

In a 250-ml three-necked flask fitted with a mechanical stirrer and a reflux condenser protected by a calcium chloride drying tube, are placed 15.1 g of methyl 3,6-dimethyl-dihydroresorcylate, 16.5 g of N-chlorosaccharin (Houben-Weyl, Methoden der Organischen Chemie Band V/3, pag. 809, 1962) and 80 ml of benzene. The reaction mixture is stirred at reflux temperature for 8 hours, cooled to room temperature and then worked up in the same manner as described in Example 11. There is obtained 9.4 g (63%) of methyl 3,6-dimethyl-resorcylate.

EXAMPLE 14

Methyl 3,6-dimethyl-resorcylate

In a 250-ml three-necked flask fitted with a mechanical stirrer and a reflux condenser protected by a calcium chloride tube are placed 9.9 g of methyl 3,6-dimethyl-dihydroresorcylate, 4.9 g 1,3-N,N-dichloro-5,5-dimethylhydantoin and 100 ml of carbon tetrachloride. The reaction mixture is stirred for 2 hours at room temperature, thereafter for an additional 7 hours at reflux temperature and then left overnight at room temperature. The reaction mixture is diluted with 100 ml of ether, stirred for 30 minutes and filtered off. The filtrate is worked up in the same manner as described in Example 11. There is obtained 7.3 g (74%) of methyl 3,6-dimethyl-resorcylate.

EXAMPLE 15

Ethyl 3,6-dimethyl-resorcylate

In a 0.5-L three-necked flask fitted with a mechanical stirrer, a thermometer and a reflux condenser protected by a calcium chloride tube, are placed a solution of 17.1 g of N-chlorocaprolactam in 50 ml of carbon tetrachloride and 24.6 g of ethyl 3,6-dimethyl-dihydroresorcylate (prepared according to the method described in Example 1; m.p. 85.0° – 86.5°C). The reaction mixture is warmed slowly, with stirring, until the appearance of an exothermic reaction, at which point the heating bath is removed. After the vigorous reaction has subsided, the heating bath is replaced and the reaction mixture is stirred at reflux temperature for an additional 3.5 hours. The reaction mixture is worked up in the same manner as described in Example 2. There is obtained 20 g (82%) of ethyl 3,6-dimethyl-resorcylate (identified by NMR, IR and mass spectral analysis): m.p. 125,5° – 127°C.

EXAMPLE 16

Methyl 3-ethyl-6-methyl-dihydroresorcylate

By substituting a mixture of 5-hepten-4-one and 6-chloroheptan-4-one (prepared from propene and butyryl chloride) for the ketone mixture of example 1, there is obtained methyl 3-ethyl-6-methyl-dihydroresorcylate; m.p. 122.5° – 123°C.

EXAMPLE 17

Methyl 3-ethyl-6-methyl-resorcylate

In a 250-ml three-necked flask fitted with a mechanical stirrer a thermometer and a reflux condenser protected by a calcium chloride drying tube, are placed a solution of 12.6 g of N-chlorocaprolactam in 100 ml of benzene and 18 g of methyl 3-ethyl-6-methyl-dihydroresorcylate. The reaction mixture is stirred at reflux temperature for 9 hours and then worked up in the same manner as described in Example 3. There is obtained 15 g (82%) of methyl 3-ethyl-6-methyl-resorcylate (identified by IR and NMR spectral analysis); m.p. 103.2° – 104.7°C.

EXAMPLE 18

Methyl 3-methyl-6-propyl-dihydroresorcylate

A solution of 18.8 g of sodium methoxide, 46.9 g of dimethyl malonate and 44.8 g of 4-octen-3-one in 160 ml of methanol is kept at reflux temperature for 8 hours. The reaction mixture is worked up in the same manner as described in Example 1. There is obtained 67.2 g (84%) of methyl 3-methyl-6-propyl-dihydroresorcylate, m.p. 112.3° – 114.1°C.

EXAMPLE 19

Methyl 3-methyl-6-propyl-resorcylate

By substituting methyl 3-methyl-6-propyl-dihydroresorcylate for methyl 3,6-dimethyl-dihydroresorcylate (Examples 2–9), there is obtained methyl 3-methyl-6-propyl-resorcylate; recrystallized from toluene m.p. 117.4° – 118.9°C.

EXAMPLE 20

Methyl 3-methyl-resorcylate

In a 1-L three-necked flask fitted with a mechanical stirrer and a reflux condenser protected by a calcium chloride drying tube, are placed a solution of 60.5 g of N-chlorocaprolactam in 400 ml of benzene and 75.5 g of methyl 3-methyl-dihydroresorcylate, prepared from 5-chloropentan-3-one (R. B. Woodward et al.; J.Am.-Chem.Soc. 74, 4223 (1952)) and dimethyl malonate; m.p. 126.5° – 127.9°C. The reaction mixture is stirred at reflux temperature for 8 hours, then cooled to 30°C, transferred to a separatory funnel and washed successively with water, 0.2 molar sodium carbonate solution and again with water. The organic layer is then cooled to 5°C and extracted with cold 0.4N sodium hydroxide solution. The aqueous solution is acidified with a slight excess of 15% hydrochloric acid. The temperature is maintained at 0°C throughout the acidification. The solid product is filtered off, washed thoroughly with water and dried, yielding 63.5 g (85%) of methyl 3-methyl-resorcylate (identified by NMR, IR and mass spectral analysis). M.p. 130.5° – 131.6°C).

EXAMPLE 21

Ethyl 3-methyl-resorcylate

In a 250-ml three-necked flask fitted with a mechanical stirrer and a reflux condenser, are placed a solution of 14.7 g of N-chlorocaprolactam in 100 ml of benzene and 19.8 g of ethyl 3-methyl-dihydroresorcylate (prepared from 5-chloropentan-3-one and diethyl malonate; m.p. 85.2° – 86.7° C). The reaction mixture is stirred at reflux temperature for 8 hours, cooled to 30°C and worked up in the same manner as described in Example 20. There is obtained 14.5 g (74%) of ethyl 3-methylresorcylate, melting at 129.1° – 129.6°C.

I claim:

1. A process for the preparation of mono- and di-alkylresorcylic esters of the general formula

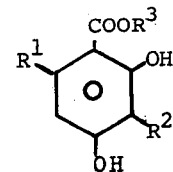

wherein $R^1$ is hydrogen or an alkyl radical containing up to three carbon atoms, $R^2$ represents an alkyl radical having up to three carbon atoms, and $R^3$ represents methyl or ethyl, which consists essentially of reacting the corresponding dihydroresorcylic esters represented by the general formula

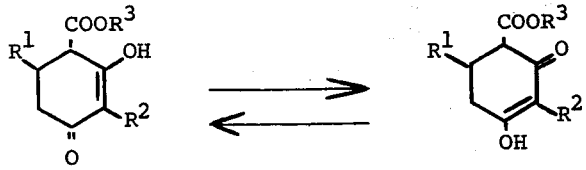

with an N-bromo- or N-chloro- derivative of an amide selected from the class consisting of acetamide, aromatic amides, caprolactam, succinimide, phthalimide, saccharin, and N,N-dihalohydantoins, in an inert solvent at a temperature between room temperature and the reflux temperature of the solvent employed.

2. The process of claim 1 wherein the haloamide is N-chlorocaprolactam.

3. The process of claim 1 wherein the haloamide is N-bromocaprolactam.

4. The process of claim 1 wherein the haloamide is N-bromosuccinimide.

5. The process of claim 1 wherein the haloamide is N-chlorosuccinimide.

6. The process of claim 1 wherein the haloamide is N,N-dichloro-dimethyl hydantoin;

7. The process of claim 1 wherein the haloamide is N-chloroacetamide.

8. The process of claim 1 wherein the haloamide is N-chlorosaccharin.

9. The process of claim 1 wherein the haloamide is N-chloro acetanilide.

10. The process of claim 1 wherin the haloamide is N-bromobenzamide.

11. The process of claim 1 wherein each of $R^1$, $R^2$ and $R^3$ is a methyl radical.

12. The process of claim 1 wherein $R^1$ and $R^2$ are each a methyl radical and $R^3$ is an ethyl radical.

13. The process of claim 1 wherein $R^2$ and $R^3$ are each a methyl radical and $R^1$ is hydrogen.

14. The process of claim 1 wherein $R^1$, $R^2$ and $R^3$ are each a methyl radical and the N-haloamide is N-chlorocaprolactam.

15. The process of claim 1 wherein $R^2$ and $R^3$ are each a methyl radical, $R^1$ is hydrogen and the haloamide is N-chlorocaprolactam.

* * * * *